United States Patent [19]

Purcell et al.

[11] Patent Number: 5,023,452
[45] Date of Patent: Jun. 11, 1991

[54] METHOD AND APPARATUS FOR DETECTING TRACE CONTAMINENTS

[75] Inventors: Lauren M. Purcell, Signal Hill; Albert F. Lawrence, San Diego, both of Calif.

[73] Assignee: Hughes Aircraft Company, Los Angeles, Calif.

[21] Appl. No.: 511,672

[22] Filed: Apr. 20, 1990

[51] Int. Cl.$^5$ ...................... G01N 23/00; G01N 31/00
[52] U.S. Cl. ..................................... 250/306; 250/304; 250/307
[58] Field of Search ............. 250/304, 306, 307, 423 F

[56] References Cited

U.S. PATENT DOCUMENTS

| | | | |
|---|---|---|---|
| 4,013,888 | 3/1977 | Macias et al. | 250/304 |
| 4,178,507 | 12/1979 | Brunnée | 250/288 A |
| 4,594,506 | 6/1986 | Ghaderi | 250/288 A |
| 4,740,298 | 4/1988 | Andresen et al. | 250/288 A |
| 4,841,145 | 6/1989 | Wada et al. | 250/304 |

Primary Examiner—Bruce C. Anderson
Attorney, Agent, or Firm—Michael W. Sales; Wanda Denson-Low

[57] ABSTRACT

Apparatus and methods for identifying the nature of an unidentified substrate present in trace amounts of known gaseous or liquid media such as air or water include collecting a sample of the substance in the media, filtering and concentrating the sample, depositing at least a portion of the same on a known substrate, analyzing the deposited sample utilizing SETM, NFOM and/or AFM techniques to form one or more images characteristic of the unidentified substance, and then identifying the substance by comparing the images so obtained to images of known substances obtained using the same techniques.

3 Claims, 1 Drawing Sheet

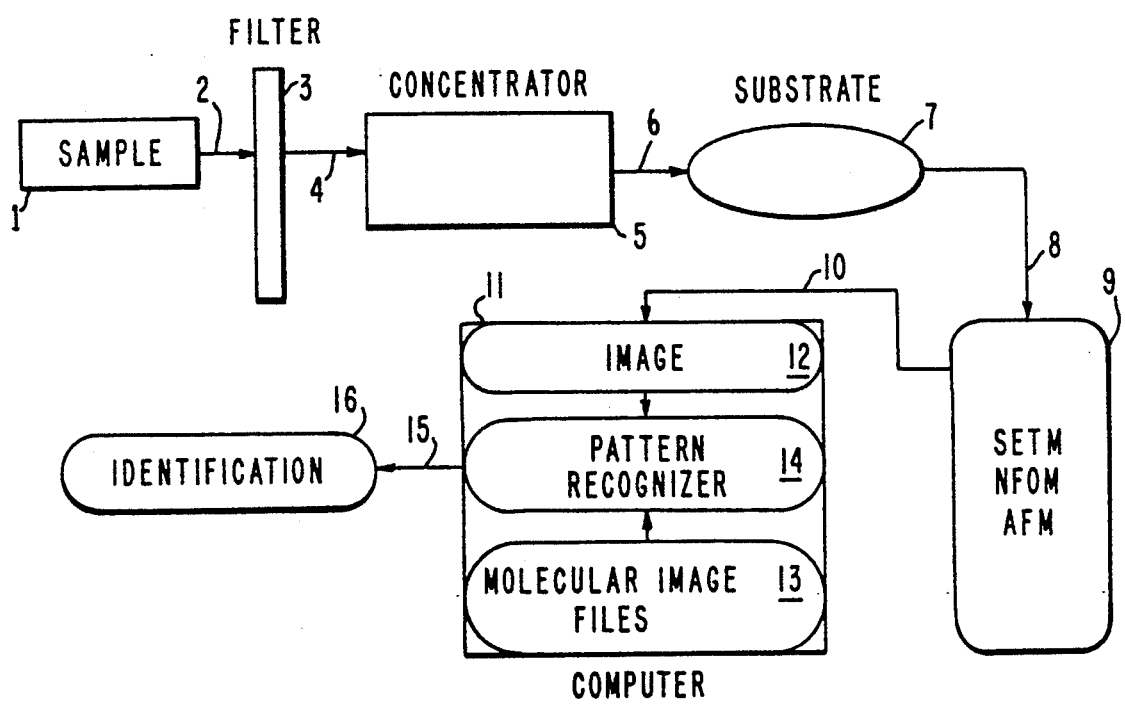

METHOD AND APPARATUS FOR DETECTING TRACE CONTAMINENTS

1. FIELD OF THE INVENTION

This invention relates to methods and apparatus for detecting trace amounts of contaminant substances in known gaseous or liquid media using scanning electron tunnelling microscope (SETM) techniques, alone, or in combination with near-field optical microscopy (NFOM) techniques and/or atomic force microscopy (AFM) techniques.

2. DESCRIPTION OF RELATED ART

Before now, trace amounts of contaminant substances such as toxic wastes, drugs and explosives have been detected, where feasible, utilizing analytic chemistry techniques, X-ray equipment, or a combination of the two. To date, no one has provided any method or apparatus for detecting and identifying a wide range of trace contaminants in media where the contaminants are present in concentrations of parts per billion or less.

3. SUMMARY OF THE INVENTION

This invention provides methods and apparatus for detecting the presence of trace amounts of an unidentified substance such as a contaminant substance in a known gaseous or liquid medium. Such apparatus can include means for collecting a sample of such a substance in such media; means for filtering the sample; means for concentrating the filtered sample; means for depositing at least a portion of the collected, filtered, concentrated sample on a known substrate; means for analyzing the filtered, concentrated sample on the substrate selected from the group consisting of scanning electron tunnelling microscope (SETM) techniques, atomic force microscope (AFM) techniques and near-field optical microscope (NFOM) techniques to form at least one image characteristic of the substance; and means for comparing the image of the unidentified substance to images of known substances to determine the nature of the unidentified substance.

The methods for identifying trace amounts of unidentified substances such as contaminant substances in known gaseous or liquid media comprise collecting a sample of the unidentified substance in such media, filtering the sample, concentrating the sample, depositing at least a portion of the sample on a known substrate analyzing the deposited sample on the substrate utilizing SETM, NFOM and/or AFM techniques to form at least one image characteristic of the unidentified substance, and comparing the image of the unidentified substance to images of known substances to identify the nature of the unidentified substance.

In these methods and apparatus, the substance can be present in concentrations of parts per billion or smaller, and can be dissolved or simply dispersed in the gaseous o liquid media. Examples of substances that can be identified using these new apparatus and methods are particles of controlled substances such as cocaine and heroin, and contaminants such as metallic particles, explosive particles, and toxic chemicals.

The gaseous or liquid media in which the trace amounts of substances may appear include air, water and other gas and liquid media whose nature and composition are known or capable of being determined.

The filtering and concentrating should be sufficient to promote adherence of a substantial number of molecules of the sample to the substrate for identification of the unidentified substance in the sample in a small number of analytical scans. To obtain optimum results, substantially all of the molecules in the sample should be deposited on the known substrate. If the sample includes substances that are not of interest, the sample may first be purified to insure that only particles of the unidentified substance of interest, and then only particles of molecular size, adhere to the substrate. Some samples, especially those in liquid media, can be filtered with micropore filters.

Several methods are available for concentrating the sample. For example, samples in a gaseous medium can be concentrated by directing a fine spray or aerosol of water through a long tube containing the gaseous medium. The water droplets absorb, and may dissolve vaporized molecules as they pass through the tube, thus concentrating volatilized, unidentified substances.

Alternatively, a gaseous medium containing an unidentified substance can be blown or otherwise directed past a series of plates held at cryogenic temperatures. Volatilized molecules of the unidentified substance in the sample precipitate on such plates. The precipitated molecules can be collected for analysis, or the plates may be scanned directly.

Another alternative calls for blowing or otherwise directing a gaseous medium containing an unidentified substance past parallel plates which are charged to a high voltage. If electrons are injected into the gaseous medium before the medium passes between the plates, large molecules are ionized, migrate to the positive plate, and can be collected for analysis. Samples of unidentified substances in liquid media can be concentrated by evaporation of one or more drops of liquid medium on the scanning substrate.

The analytical devices used in the methods and apparatus of this invention include scanning electron tunnelling microscopy, atomic force microscopy and near-field optical microscopy. These techniques are described in such published articles as: *Scanning Near-Field Optical Microscopy* By D. W. Paul, et al., General Microscopy, volume 152, Part 3, December 1988, pages 853–861; *Scanning Tunnelling Microscopic Images of Amino Acids*, General Microscopy, volume 152, Part 3, December 1988, pages 811–816 and *Scanning Tunnelling Microscopy and Atomic Force Microscopy; Application to Biology and Technology* by P. K. Hansma, et al., Science Magazine, Oct. 14, 1988, volume 242, pages 209 and following.

The images of the substance or substances detected in the sample are, in preferred embodiments, converted to digitized signals or patterns, and compared to digitized signals from images of known substances made using SETM, NFOM and/or AFM techniques. The images of the unidentified substance are compared to images of known substances to determine the nature of the unidentified substance.

BRIEF DESCRIPTION OF THE DRAWING

The methods and apparatus of this invention can better be understood by reference to the drawing which provides a schematic flow diagram of a preferred embodiment of this invention.

DESCRIPTION OF THE PREFERRED EMBODIMENT

In the drawing, a collected sample 1 of an unidentified contaminant substance such as a toxic chemical dispersed or dissolved in a known gaseous or liquid medium such as air or water is conveyed on path 2 to filtering means 3. There, the sample 1 is filtered, and conveyed on path 4 to concentrator 5. In concentrator 5, the sample is concentrated, as by boiling or centrifuging, and then passes on path 6 for deposition on known substrate 7.

The deposited sample on substrate 7 is then conveyed on path 8 to analysis by one or more of the SETM, NOFM or AFM devices 9, and the resulting images are conveyed on path 10 to computer 11. There, the image of the unidentified sample 12 is compared to images of known substances from computer memory 13 by pattern recognizer 14. Upon recognition of the image of the unidentified substance, its nature is conveyed on path 15 for display at station 16.

What is claimed is:

1. An apparatus for identifying the nature of an unidentified present in trace amounts substance in a known gaseous or liquid medium comprises:
    means for collecting a sample of said unidentified substance in said media; means for filtering said sample; means for concentrating the filtered sample to form a filtered concentrated sample; means for depositing at least a portion of said filtered, concentrated sample on a known substrate; means for analyzing the filtered, concentrated deposited sample on said substrate selected from SETM, NFOM and AFM means to form at least one image characteristic of said unidentified substance; and means for comparing said at least one image to images of known substances from SETM, NFOM and AFM analysis to identify said substance.

2. A method for identifying the nature of an unidentified substance in a known gaseous or liquid medium comprises collecting a sample of said substance in said media; filtering said sample to form a filtered sample; concentrating said filtered sample to form a filtered, concentrated sample; depositing at least a portion of said filtered concentrated sample on a known substrate; analyzing the filtered, concentrated sample on said substrate utilizing at least one of the SETM, NOFM and AFM techniques to form at least one image characteristic of the substance; and identifying the substance from said at least one image.

3. The method of claim 2 further comprising comparing said image to images of known substances derived from analyzing known such substances by SETM NOFM and/or AFM techniques.

* * * * *